(12) United States Patent
Greenwald

(10) Patent No.: US 8,529,469 B2
(45) Date of Patent: Sep. 10, 2013

(54) FECAL EXAMINATION METHOD AND COLLECTION CONTAINER

(76) Inventor: Robert J. Greenwald, Venice, FL (US)

( * ) Notice: Subject to any disclaimer, the term of this patent is extended or adjusted under 35 U.S.C. 154(b) by 392 days.

(21) Appl. No.: 12/884,542

(22) Filed: Sep. 17, 2010

(65) Prior Publication Data

US 2011/0020860 A1    Jan. 27, 2011

Related U.S. Application Data

(63) Continuation-in-part of application No. 12/345,119, filed on Dec. 29, 2008, now abandoned.

(51) Int. Cl.
*A61B 5/00* (2006.01)
*B65D 81/00* (2006.01)
*A61M 1/00* (2006.01)

(52) U.S. Cl.
USPC ............................ 600/573; 604/317; 604/318

(58) Field of Classification Search
USPC .................................. 600/573; 604/317–357
See application file for complete search history.

(56) References Cited

U.S. PATENT DOCUMENTS

| | | |
|---|---|---|
| 3,761,408 A | 9/1973 | Lee |
| 3,819,045 A | 6/1974 | Greenwald |
| 4,007,012 A | 2/1977 | Greenwald |
| 4,032,437 A | 6/1977 | Greenwald |
| 4,225,423 A | 9/1980 | Cotey |
| 4,288,316 A * | 9/1981 | Hennessy ....................... 209/17 |
| 4,293,405 A | 10/1981 | Greenwald |
| 4,318,803 A | 3/1982 | Holmgren |
| 4,559,837 A | 12/1985 | Cerqueira |
| 5,066,463 A | 11/1991 | Chang |
| 5,431,884 A | 7/1995 | McDonough et al. |
| 5,624,554 A * | 4/1997 | Faulkner et al. ............... 210/232 |
| 7,264,780 B1 | 9/2007 | Sanner |
| 7,338,634 B2 * | 3/2008 | Chang .......................... 422/408 |
| 2004/0179976 A1 | 9/2004 | Chang |
| 2006/0122534 A1 | 6/2006 | Matsumura et al. |
| 2007/0269341 A1 | 11/2007 | Halverson et al. |
| 2008/0210619 A1 | 9/2008 | Lapenna |

FOREIGN PATENT DOCUMENTS

EP        0175326 A2    3/1986

* cited by examiner

*Primary Examiner* — Sean Dougherty
*Assistant Examiner* — Devin Henson
(74) *Attorney, Agent, or Firm* — Long Technology Law, LLC; Joseph Long

(57) ABSTRACT

A method for conducting a fecal examination includes providing a collection spoon and a collection container comprising a transparent body having a cap which can be removed to permit fecal matter to be received in the collection container with the spoon to be mixed with a flotation material to aid in separating the fecal matter and ova or eggs of parasites that may be contained in the fecal matter and then dispensed through a filter mounted in the cap of the collection container to a test tube and a cover slip on the test tube for examination of the filtered material for the presence of the ova of parasites.

12 Claims, 4 Drawing Sheets

FECAL EXAMINATION METHOD AND COLLECTION CONTAINER

CROSS-REFERENCE TO RELATED APPLICATIONS

This application is a Continuation-in-part of application Ser. No. 12/345,119 filed on Dec. 29, 2008.

FIELD OF THE INVENTION

The present invention relates to a method of preparing fecal matter for examination by providing a collection container and a method of using the collection container for separating the feces from ova that might be contained in the fecal matter.

BACKGROUND OF THE INVENTION

The examination of fecal matter to determine whether or not the ova or eggs of parasites are present generally includes the steps of collecting feces and then adding a solution of the proper specific gravity to the fecal material to provide a fecal emulsion. The ova in the emulsion can then be separated from the emulsion due to their difference in specific gravity. The separated ova then can be examined to determine the necessary treatment. Examination can be made by placing the separated material on a slide and examining the material under a microscope. This method is generally referred to as the passive flotation process.

In another known method the mixture is put in a centrifuge and the lighter ova are separated from the fecal matter by action of the centrifuge. Again the separated ova are examined by a microscope. This method of examination is generally referred to as the centrifuge flotation process.

Published Patent application US 2007/0269341 A1 by Halverson et al discloses "A Sampling Assembly and Method of Preparing Samples" which utilizes agitation to accomplish the desired separation of microorganisms from a solution. The Halverson application doesn't disclose the use of a passive flotation system to cause the microorganisms to rise to the top and agitation alone will not effectively separate ova from fecal matter to permit examination of the ova. Actual pressure on the fecal matter to break up the fecal matter is required. Equally important certain types of agitation such as those disclosed in Halverson are contraindicated due to the accumulation of unwanted air bubbles in the emulsion.

SUMMARY OF THE INVENTION

The present invention provides both a method for preparing fecal matter for examination by separating the ova and feces and an improved collection container for use in the method. The method can be used to prepare the fecal matter for examination using either the passive flotation process or the centrifuge flotation process. In practicing the method of the present invention fecal matter is deposited in the collection container. A solution of the proper specific gravity is added to the collection container and the fecal matter and a cap is provided to close the container. The solution is selected to have a specific gravity in the range of 1.22 to 1.40 to aid in causing the separated lighter ova to rise in the solution. The method of preparing the fecal matter for examination and the use of the collection container of the present invention is useful in examination of the ova either by the passive flotation process or the centrifuge flotation process.

The collection container is uniquely constructed of a pliable, transparent material that permits the sides of the collection container to be squeezed together to substantially touch to engage and thereby break up the fecal matter. The transparent sides permit monitoring the mixing. The cap is provided with a spout and in one form of the invention a breakaway opening in the spout. A filter is mounted in the cap so that pouring the contents from the collection container will permit passage of the ova and smaller particles of fecal matter but will prevent the larger remaining fecal matter from being poured from the collection container. The ova then can be further separated from the remaining material by using either the passive flotation method or by using the centrifuge flotation method and then examined under a microscope. This provides a fecal examination method in which direct contact with the fecal matter is not necessary prior to the actual examination thus substantially eliminating unpleasant contact by humans during the process.

By actually breaking up the fecal matter while it is in the collection container the ova are effectively released from the fecal matter so that ova will be in the emulsion that is examined whether the passive flotation process or the centrifuge flotation process is employed prior to examination.

BRIEF DESCRIPTION OF THE DRAWINGS

A better understanding of the present invention will be achieved by referring to the drawings wherein.

DETAILED DESCRIPTION OF THE PREFERRED EMBODIMENTS

Figures 1, 2:
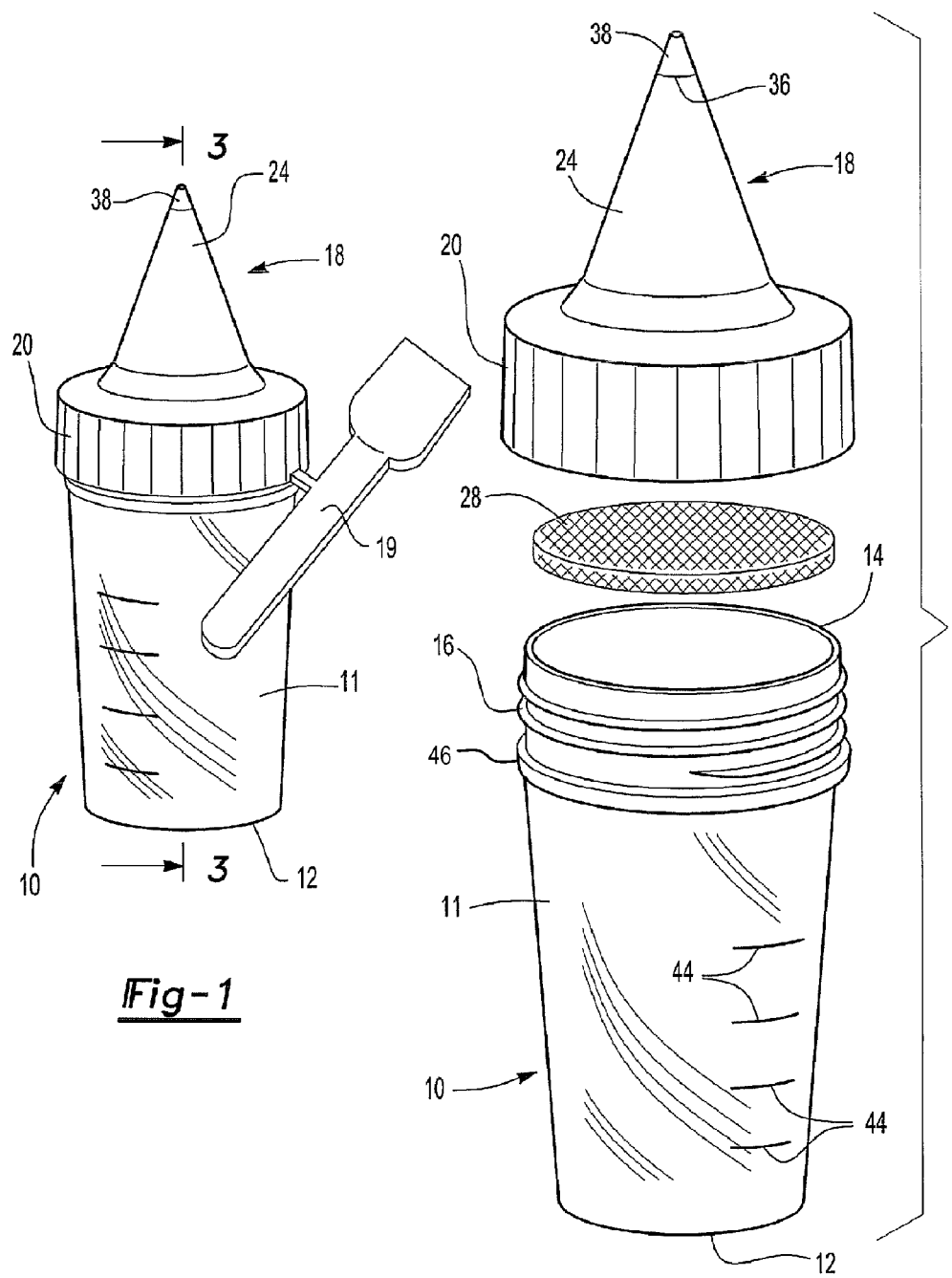
FIG. 1 is an elevational view of the fecal collection container of the present invention.
FIG. 2 is an exploded elevational view of the collection container shown in FIG. 1.
Figure 3:
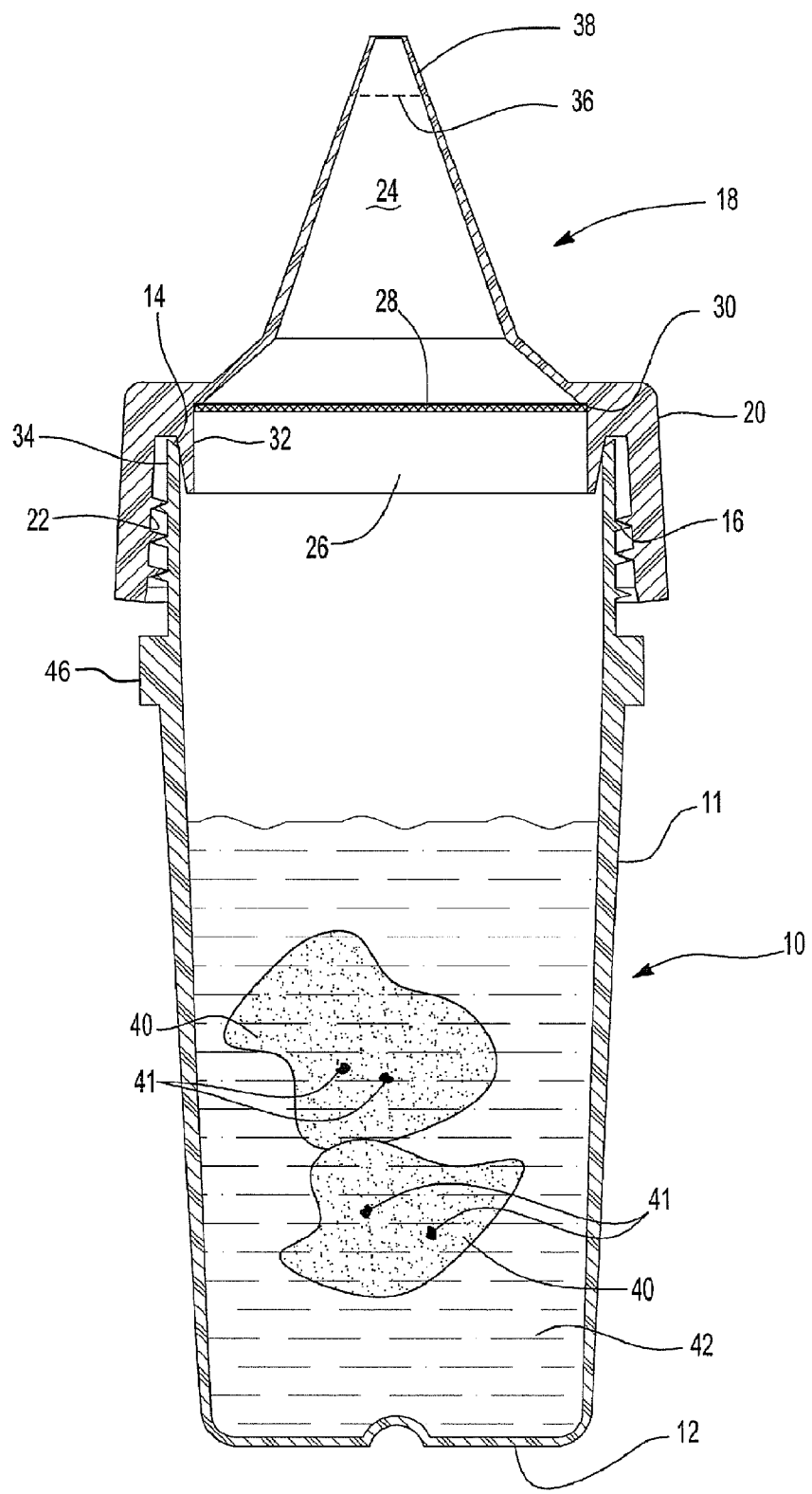
FIG. 3 is a cross sectional view taken substantially along line 3-3 of FIG. 1.

Now referring to the drawings, FIG. 1 illustrates the preferred collection container 10 of the present invention as being substantially cylindrical and as best seen in FIG. 3, having sides 11, a closed flat bottom 12 and as best seen in FIG. 2 an open top 14 provided with an outer screw thread 16. A spoon 19 is detachably secured to the collection container 10. A cap 18 is adapted to close the open top 14 by being screwed unto the thread 16.

As best seen in FIG. 3 the cap 18 includes a base 20 having internal threads 22 for receiving the threads 16 for screwing the cap 18 on and off the collection container 10 and a spout 24 that extends from an opening 26 formed in the base 20. A filter 28 is mounted in the spout 24 by being urged against a flange 30 by a downwardly extending flange 32 formed in the cap 18. The flange 32, being formed of a resilient plastic material, urges the filter 28 against the flange 30 and to remain in place when snapped into the cap 18. The flange 32 also engages a top edge 34 of the open top 14 of the collection container 10 to effectively seal the connection between the collection container 10 and the cap 18 when the cap 18 is tightened against the top edge 34 of the collection container 10. This construction limits distortion of the open top 14 when the sides 11 are squeezed together as will be subsequently described. As can best be seen in FIG. 2 the cross-sectional area of the top opening 14 of the container 10 is larger than the cross-sectional area of the bottom 12 to provide easier access for depositing the fecal matter 40 in the container 10. The spout 24 may be provided with a weakened section 36 to permit removal of a top portion 38 of the spout 24 to provide for pouring materials into and out of the collection container 10.

FIG. 3 illustrates the collection container 10 partially in cross-section to more clearly illustrate the contents of the collection container 10 during a step in the fecal examination process. Fecal matter 40 containing ova 41 has been deposited in the container 10 preferably using the detached spoon. A solution 42 is then introduced into the collection container 10. Solutions for urging the ova 41 to rise to the top of the collection container 10 are well known in fecal examination methods and generally have a specific gravity of 1.22 to 1.40 which is greater than that of the ova 41. The collection container 10 is preferably constructed of a transparent material so that the fecal matter 40 and solution 42 will be visible through the sides 11 of the collection container 10. To prepare for the reception of the solution 42 the cap 18 is removed from the top 14 of the collection container 10 and the solution 42 is poured into the collection container 10 to mix with the previously deposited fecal matter 40. If preferred, the portion 38 of the cap 18 can be removed either by breaking at the score line 36 or with a nail trimmer (not shown) or the like and the solution 42 poured into the collection container 10 through the spout 24. The collection container 10 is not completely filled with solution 42 for mixing the fecal matter 40 with the solution 42. Marks 44 (FIG. 2) on the side 11 of the container 10 act as guides to aid in determining the proper amount of solution 42 to be added to the container 10. If the spoon 19 hasn't already been deposited in the container 10 after the collection of the fecal matter 40 it is now deposited in the container 10. Depositing the spoon 19 in the container 10 will not adversely affect the practice of the method of the present invention and in fact it may actually aid in the separation of ova 41 from the fecal matter 40.

Figure 4:
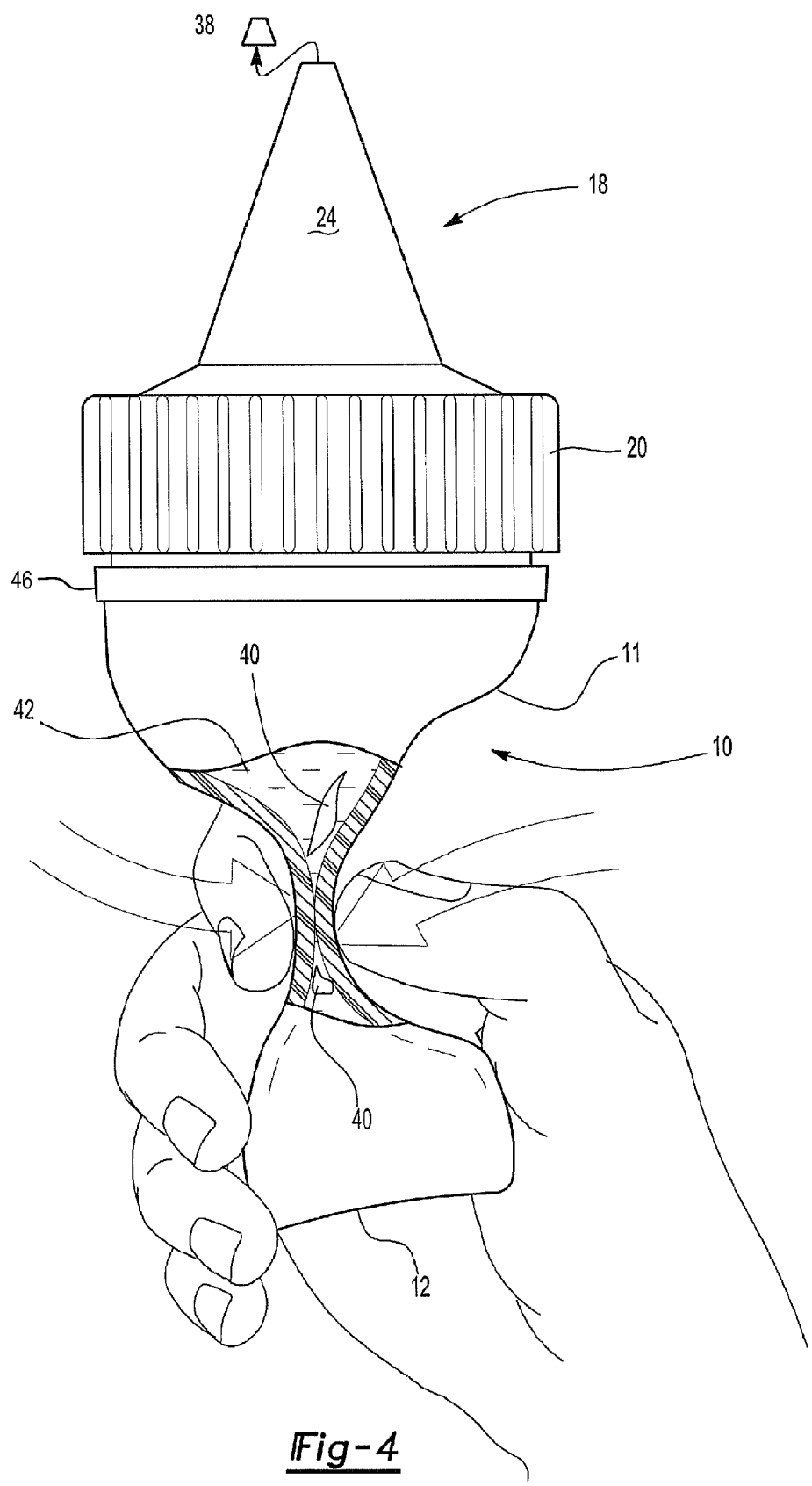
FIG. 4 is an elevational view of the collection container of the present invention partially in section and illustrating use of the collection container to break up the fecal matter.

The material used for the sides 11 of the collection container 10 is pliable with a memory so that the fecal matter 40 can be broken up and mixed with the solution 42 by squeezing the sides 11 of the collection container 10 together to mash the fecal matter 40 into the solution 42 to form an emulsion of fecal matter 40, ova 41 and fecal matter 42. As best seen in FIG. 4 the material used for the collection container 10 is sufficiently pliable that the sides 11 of the container can be squeezed together so that they actually touch thereby insuring that the fecal matter 40 caught between the sides 11 can be broken into small pieces. The material used for the sides 11 of the container 10 has sufficient memory that the sides 11 will upon release return to substantially their original shape. To insure this return and to prevent distortion of the top 14 of the collection container 10 a stiffening band 46 is provided. The stiffening band 46 and the portion of the collection container 10 above the stiffening band 46 are constructed of stiffer material than the sides 11 of the collection container 10 thereby insuring that the top 14 of the collection container 10 will not be distorted during the squeezing process and the cap 18 will remain tightly in place sealing against spillage. The construction of the flange 32 and the manner which it with which extends internally of the top 14 to capture the top edge 34 between the flange 32 and the base 20 of the cap 18 further limit distortion of the top 14.

The solution 42 provides for flotation or levitation of parasite eggs or ova 41 and the like introduced into the solution 42 with the fecal matter 40 so that ova 41 will have tendency to rise to top of the solution once it is broken away from the rest of the fecal matter 40. The solution 42 can consist of sodium nitrate or sucrose, or magnesium sulfate, or zinc sulfate, sodium chloride or other solutions the purpose of which is to raise the specific gravity to range of 1.22 to 1.40 so that the ova 41 that separates from the fecal matter 40 as the fecal matter 40 is mashed by squeezing the sides of the collection chamber 10 together are lighter than the solution 42 and will therefore rise to the top of the solution 42. Providing a collection container 10 which provides for breaking up the fecal matter 40 while it is in the container 10 is an important feature of the present invention. It should be clear that agitation will not adequately break up the fecal matter 42 and could result in unwanted and detrimental air bubbles.

Once the fecal matter 40 has been broken into small pieces so that the ova 41 has floated to the top of the solution 42 and the upper portion 38 of the spout 24 has been removed a portion of the solution 42 containing the fecal matter 40 and ova 41 is poured out of the collection container 10 to be examined. The filter 28 limits the size of the material permitted to flow from the collection container 10 with the solution 42.

Figure 5:
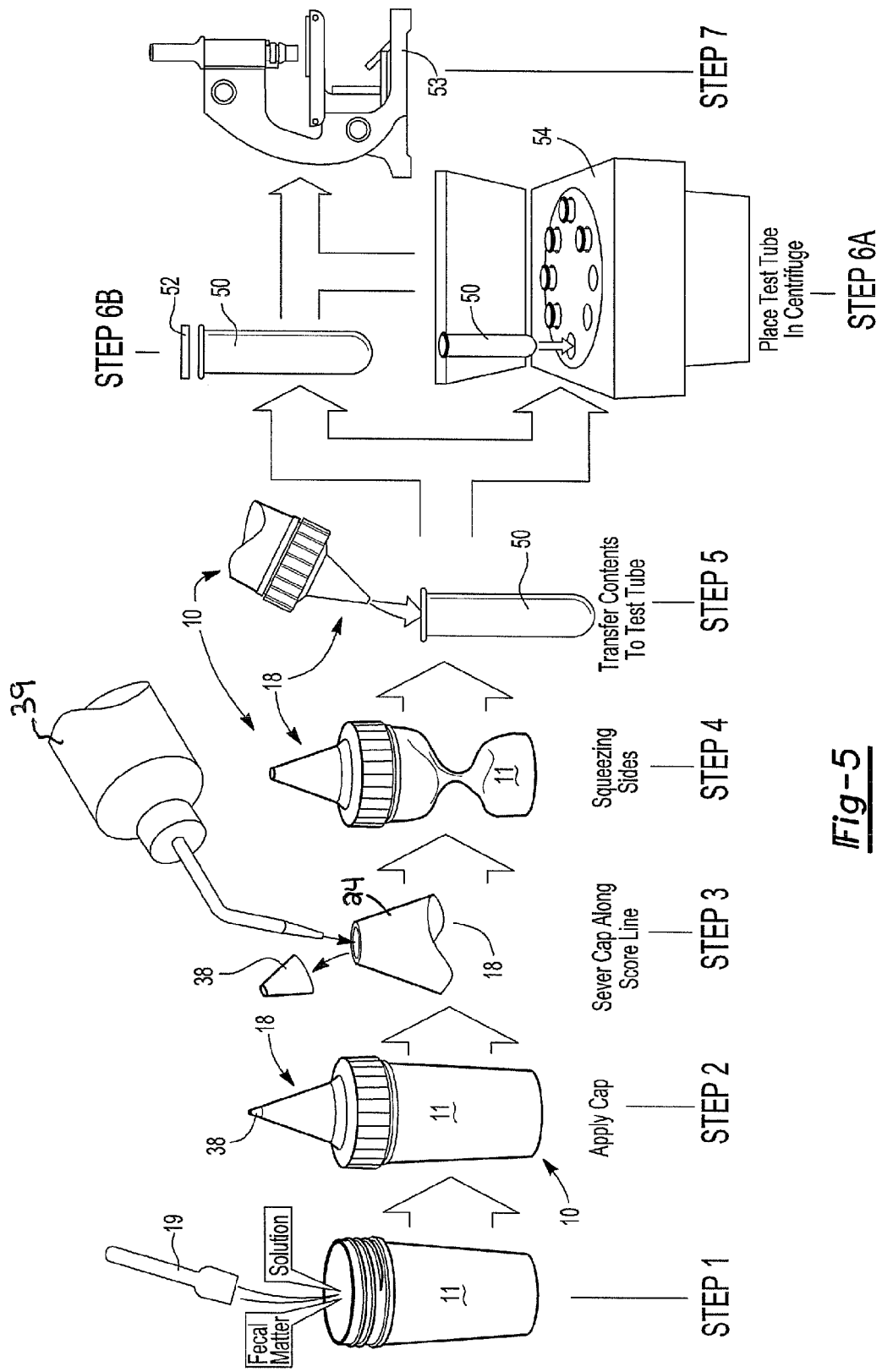
FIG. 5 is a diagrammatic view illustrating the steps in the method of the present invention.

FIG. 5 is a diagrammatic illustration of the steps in practicing the method of the present invention. It should be apparent that the collection container 10 and the capability of the sides 11 of container 10 to be squeezed together to mash the fecal matter 40 in the solution 42 to separate the ova 41 from the fecal matter 40 is an important part of the method of the present invention The fecal matter 40 is collected and is deposited in the collection container 10 using the spoon 19 (FIG. 1). The spoon 19 has been detached from the collection container 10 to be used to collect the fecal matter 40. The spoon 19, after use, can be deposited in the collection container 10 for disposal later. It will not interfere with the preparation of an examination sample and it provides a convenient and clean way of disposing of the spoon 19.

The solution 42 can be added to the collection container 10 through the open container chamber 10 at this stage or the cap 18 can be tightened and the upper portion 38 of the cap 18 removed and the solution 42 added through the spout 24. If the solution 42 is to be added though the spout 24 then a wash bottle 39 (FIG. 5, Step 3) should be used. A wash bottle is a bottle that has fluid in it and when squeezed the fluid comes out in a very fine hose like projection.

The marks 44 on the side 11 of the collection container 10 will aid in determining the amount of solution 42 to add. As best be seen in Step 4 of FIG. 5 the fecal matter 40 is mashed into little pieces in the container by squeezing the sides 11 of the collection container 10 together. As shown in Step 3 the spout 24 has to be opened at this stage or an air lock will be created which would prevent squeezing of the collection container 10.

The solution 42 and the fecal matter 40 are then filtered by filter 28 (FIG. 2) as it is poured from the spout 24 of the collection container 10 into a tube 50. If the passive flotation method is to be used to separate the ova 41 from the fecal matter 40 a cover slip 52 is placed over tube 50 as shown in Step 6A and the ova 41 are given sufficient time to float to the top of the tube 50 and adhere to the underside of the cover slip 52. The cover slip 52 is then removed and placed under a microscope 53 (Step 7) to examine the ova 41.

The preferred method however is to use a centrifuge 54 (Step 6A) to insure that a suitable sample is obtained. As shown in Step 5 and 6B the tube 50 can be filled as indicated above and then placed in the centrifuge 54 but it is preferred that the tube 50 be placed in the centrifuge 54 and then filled. In either event the tube 50 is filled to the top to form a meniscus. The cover slip 52 is placed on the tube 50 and the centrifuge 54 is operated to cause a sample with ova 41 to adhere to the underside of the cover slip 52. The cover slip 52 is then removed for examination under the microscope 53.

It should be apparent that although use of the method and the collection container of the present invention will most often be used as a part of the examination process for examining the feces of animals such as dogs and cats for the presence of worms and other parasites it will also find use in the examination of animal feces and human feces for other purposes.

It should also be apparent that the present invention provides a collection container for use in the fecal matter examination process that eliminates several steps in the processes presently employed. A disposable collection container as well as a collection spoon is provided for depositing the feces in the container and for mixing the fecal matter with the solution that does so with a minimum of exposure to the fecal matter by the examiner. An empty collection container can be provided to the animal owner or the patient and the collection container can be used to deliver the specimen to the examiner with the collection spoon in the container. The examiner can then add the solution and, after mixing, remove the top of the spout and pour out the small amount of ova and solution to permit examination. The collection container then, with the remaining contents including the spoon, can be discarded.

Although the examination process has been described as including examination of the separated material by microscope on a slide after the ova has been permitted to float to the top of a container it should be understood that the collection container has utility in a process in which a centrifuge is used. The material can be deposited through the spout to a test tube for use in the centrifuge. With either use a collection container has been provided for fecal examination that minimizes human contact with the material being examined.

While the collection containers 10 has been described as being constructed of a transparent material it should be apparent that a translucent material could be used to construct the sides of the collection containers as well. All that is necessary is that the fecal matter be sufficiently visible to permit locating the material to permit it to be mashed by squeezing the sides of the collection container together.

It should also be apparent that changes could be made to the collection container and the method of use as described herein without departing from the spirit of the invention as set forth in the following claims.

The invention claimed is:

1. A method for examining fecal matter comprising steps of:
   providing a container for receiving fecal matter, the container comprising a closed bottom, an open top, and sides constructed of a sufficiently pliable material to permit the sides of the container to be squeezed into contact with each other;
   introducing fecal matter into the container;
   introducing a flotation solution into the container;
   squeezing the sides of the container together substantially into contact with each other thereby mashing the fecal matter between the sides of the container in order to break up the fecal matter;
   dispensing a mixture of the fecal matter and the flotation solution from the container; and
   examining the mixture under a microscope.

2. The method of claim 1, further comprising a step of filtering the mixture while dispensing the mixture from the container.

3. The method of claim 1, wherein dispensing the mixture comprises dispensing the mixture into a tube and using a centrifuge to cause a material within the mixture to rise in the tube.

4. The method of claim 3, wherein the material comprises ova of parasites.

5. The method of claim 1, wherein the container further comprises a spout, wherein a portion of the spout can be removed to provide access to the container.

6. The method of claim 1, wherein a cross-section of the open top of the container is larger than a cross-section of the closed bottom of the container.

7. The method of claim 1, wherein the container further comprises a stiffening band positioned near the open top of the container to limit distortion of the open top of the container in response to squeezing the sides of the container together substantially into contact with each other.

8. A method for examining fecal matter, the method comprising steps of:
   providing a container for receiving fecal matter, the container comprising a closed bottom, an open top, a cap removably covering the open top, and sides constructed of a sufficiently pliable material to permit the sides of the container to be squeezed substantially into contact with each other;
   introducing fecal matter into the container;
   introducing a flotation solution into the container, the flotation solution having a specific gravity to support floatation of parasite ova;
   squeezing the sides of the container substantially into contact with each other thereby mashing the fecal matter between the sides of the container in order to break up the fecal matter and release parasite ova potentially located within the fecal matter;
   dispensing a mixture of the fecal matter, the flotation solution, and the parasite ova from the container; and
   examining the mixture.

9. The method of claim 8, wherein the container further comprises a filter disposed within the cap, and wherein dispensing the mixture comprises filtering the mixture through the cap.

10. The method of claim 8, further comprising a step of allowing the parasite ova to float into a top portion of the mixture, and wherein examining the mixture comprises selecting a sample of the mixture from the top portion of the mixture.

11. The method of claim 8, further comprising a step of centrifuging the mixture to separate the parasite ova into a portion of the mixture, and wherein examining the mixture comprises selecting a sample of the mixture from the portion of the mixture.

12. The method of claim 8, further comprising a step of centrifuging the mixture causing the parasite ova to adhere onto a cover slip, and wherein examining the mixture comprises examining the cover slip using a microscope.

* * * * *